United States Patent [19]

Saito et al.

[11] Patent Number: 4,458,683
[45] Date of Patent: Jul. 10, 1984

[54] FOCAL POINT DIRECT OBSERVATION TYPE LASER SCALPEL DEVICE

[75] Inventors: Mitsunori Saito; Shiro Sakuragi; Kyoshiro Imagawa, all of Kyoto, Japan

[73] Assignees: Agency of Industrial Science & Technology; Ministry of International Trade & Industry, both of Tokyo, Japan

[21] Appl. No.: 355,311

[22] Filed: Mar. 5, 1982

[30] Foreign Application Priority Data

May 26, 1981 [JP] Japan .................................. 56-78644

[51] Int. Cl.³ ............................................. A61B 17/16
[52] U.S. Cl. .................................................... 128/395
[58] Field of Search ..................... 128/395, 303.1, 654, 128/665, 664; 219/121 L, 121 LM; 356/318–325

[56] References Cited

U.S. PATENT DOCUMENTS

| 3,710,798 | 1/1973 | Bredemeier | 128/395 X |
| 3,750,670 | 8/1973 | Palanos et al. | 128/395 X |
| 3,796,220 | 3/1974 | Bredemeier | 128/395 X |
| 4,141,362 | 2/1979 | Wurster | 128/395 X |
| 4,266,547 | 5/1981 | Komiya | 128/395 X |
| 4,266,549 | 5/1981 | Kimura | 128/395 X |
| 4,299,229 | 11/1981 | Enderby | 128/395 |

Primary Examiner—John D. Yasko
Attorney, Agent, or Firm—Oblon, Fisher, Spivak, McClelland & Maier

[57] ABSTRACT

A focal point direct observation type laser scalpel device has a construction wherein laser beams generated by an infrared laser generator and transmitted through an optical fiber adapted for infrared laser beams and visible rays issued from a visible ray source and transmitted through optical fibers adapted for visible rays are passed through one common converging lens system so that recognition of the focal point of the laser beams is accomplished by visual observation of the focal point of the visible rays.

3 Claims, 3 Drawing Figures

FOCAL POINT DIRECT OBSERVATION TYPE LASER SCALPEL DEVICE

BACKGROUND OF THE INVENTION

This invention relates to a laser scalpel device making use of infrared laser beams which are invisible rays, and more particularly to a focal point direct observation type laser scalpel device having transmission paths for laser beams formed of fibers adapted for infrared rays.

In laser scalpel devices used for surgical operations or laser fabricating devices (hereinafter collectively referred to as "laser scalpel devices"), used for cutting, boring, and joining metallic materials, wooden materials, fabrics and paper, the infrared laser beams, on reaching the end of the transmission path, are injected into the converging lens system and are then converged (focused) at a specific position on the output side of the converging lens system. This position of convergence or focal point constitutes itself the site at which the density of the energy of the infrared laser beams is highest. For this energy to be efficiently used, therefore, the focal point is desired to be capable of being visually recognized by the user or operator of the laser scalpel device.

Since the laser beams are invisible infrared rays, however, the operator is unable to see and tell in advance where the laser beams are focused.

With a view to eliminating this disadvantage, Japanese Patent Application Disclosure Sho 52(1977)-61387 discloses a method for enabling the focal point of laser beams to be recognized by using the infrared laser beams in combination with visible rays. This method utilizes a mirror type guide path for infrared laser beams. The guide path, therefore, causes two visible guide rays to intersect with each other at the focus of a converging lens system on the premise that the focal point of the infrared laser beams coincides with the focus of the converging lens system.

This method, however, has the following drawbacks.

(i) The point at which the two visible guide rays intersect with each other has the highest luminance. The high luminance enables the operator to perceive the focus of the converging lens system but does not permit him to perceive the focal point of the infrared laser beams except in special cases. Generally on the assumption that the image of an object placed at a distance of "a" from a converging lens having a focal distance of "f" is focused at a position separated by a distance of "b" from the aforementioned converging lens, the relation among "a", "b", and "f" is expressed as follows.

$$1/a + 1/b = 1/f \quad (1)$$

In this case, the focus "F" and the focal point "P" coincide with each other when the distance "a" is infinite, namely the incident rays of the converging lens are parallel. This condition occurs only when the transmission path for infrared laser beams is of a junction mirror type. When fibers adapted for infrared rays are used as the transmission path, for example, the distance "a" generally is given a finite value. The device for indicating the focus "F" of the converging lens is utterly meaningless in the laser scalpel device which utilizes fibers adapted for infrared rays as the guide path. Conversely it may prove to be rather harmful in respect that no means is used to indicate the point at which the density of energy is highest.

(ii) Although the device for intersecting two visible guide rays is utilized for the indication of the focus, the intersection of ordinary visible rays cannot produce luminance enough to be visually discerned. For the point of intersection of guide rays to produce sufficient luminance, there must be used guide rays of high directivity. Thus, adoption of visible laser beams is inevitable.

(iii) Since this method relies on the intersection of guide rays to indicate the focus, it is inevitably required to use means for producing two or even more guide rays.

Japanese Patent Application Disclosure Sho 55(1980)-78951 discloses a method which, similarly to the method described above, utilizes a mirror type guide path for infrared rays and, on the premise that the focus and the focal point of infrared laser beams coincide with each other, conducts visible rays through a plurality of optical fibers and causes them to illuminate the focus of infrared laser beams or the surrounding area of the focus. Unfortunately, visible rays departing from optical fibers generally fail to form parallel rays or converging rays. On the contrary, they tend to diverge. For such guide rays to be focused therefore, it becomes necessary to utilize an additional lens to be exclusively used for focusing them. Installation of converging lens at the leading end of each of the plurality of optical fibers, however, adds to the size and complexity of the laser scalpel device and renders the handling of the device difficult.

SUMMARY OF THE INVENTION

An object of this invention is to provide a laser scalpel device which utilizes optical fibers for the transmission of both infrared rays and visible guide rays and, thereby, ensures clear indication of the focal point of infrared rays at which the density of energy of infrared rays is highest.

Another object of this invention is to provide a laser scalpel device compact and simple in construction and easy to handle.

To accomplish the objects described above according to the present invention, there is provided a laser scalpel device which comprises an infrared laser generator, an infrared ray grade optical fiber for transmitting laser beams issuing from the infrared laser generator, a visible ray source, visible ray grade optical fibers for transmitting visible rays issuing from the visible ray source, and a converging lens system adapted to converge both the laser beams and the visible rays in such a manner that the focal point of laser beams can be recognized by the observation of the focal point of visible rays.

In accordance with this invention, since the focal point of infrared laser beams which has the highest density of energy is recognized owing to the focal point of visible rays as described above, the recognition of the focal point of infrared laser beams can be easily accomplished with unaided eyes and the operation of the laser scalpel device, therefore, can be performed accurately and safely. Moreover, the fact that the infrared rays and the visible rays are transmitted through independent optical fibers and then converged through one common converging lens system contributes to greatly simplifying the construction of the device.

The other objects and characteristics of this invention will become apparent from the further disclosure of the invention to be made hereinbelow with reference to the accompanying drawings.

DESCRIPTION OF PREFERRED EMBODIMENT

Figure 1:
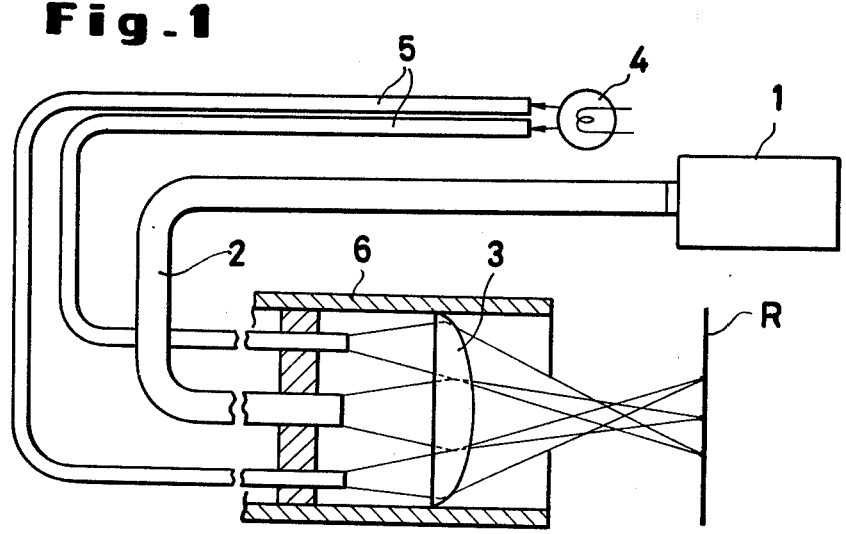
FIG. 1 is an explanatory diagram illustrating one embodiment of the focal point direct observation type laser scalpel device of this invention.

FIG. 1 is a schematic diagram illustrating a typical laser scalpel device according to the present invention. To one end of an infrared ray grade fiber 2 is connected a known infrared laser generator 1 capable of generating a $CO_2$ laser or CO laser beam. The other end of the fiber 2 is inserted into a lens barrel 6 serving as a laser scalpel and fastened in position as directed toward the opening of the lens barrel. The optical fibers 5 adapted for visible rays are similarly connected at one end thereof to a visible ray source 4 and fastened at the other end within the lens barrel 6 as directed toward the opening of the lens barrel and separated by a prescribed distance from the optical fiber 2. Although the present embodiment is illustrated as using two optical fibers for visible rays, the number of such optical fibers is not specifically limited. So far as there is used at least one optical fiber, the transmission of visible rays can be effected as required. In front of the terminal faces of the optical fibers 2, 5 inserted into the lens barrel 6, there is disposed a converging lens system 3 so that the rays and beams departing from the optical fibers 2, 5 may enter the lens.

In the construction described above, the infrared laser beams generated by the infrared laser generator 1 are transmitted through the optical fiber 2 and passed into the converging lens system 3. In the meantime, the visible rays issuing from the visible ray source 4 are transmitted through the optical fibers 5. The leading ends of these optical fibers 5 and the leading end of the optical fiber 2 are fastened within the lens barrel 6 at positions approximating each other. The visible rays which have been transmitted through the optical fibers 5, therefore, are passed into the same converging lens system 3 as the infrared laser beams. Within the lens barrel 6, the leading end of the optical fibers 5 are fastened in such a manner that the focal point of the visible rays brought in through the optical fibers 5 may assume a specific positional relation with the focal point of the infrared laser beams as will be more fully described afterward.

As optical fibers for the transmission of infrared laser beams, any of known optical fibers using cores made of halogenides such as TlBr, AgBr, and AgCl. For the transmission of visible rays, optical fibers using cores made of quartz glass can be used, for example.

Figure 2:
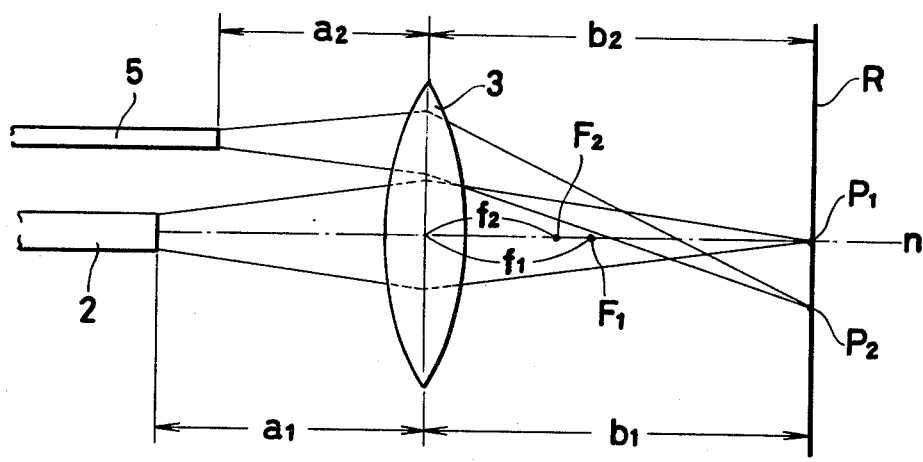
FIG. 2 is an explanatory diagram illustrating the condition of convergence of infrared laser beams and visible rays through the converging lens system in the device of FIG. 1.

In accordance with this invention, since the infrared laser beams and the visible guide rays are transmitted through optical fibers 2, 5 as described above instead of a mirror type guide path, the beams and rays are diverged at a fixed angle as illustrated in FIG. 2 at the moment that they cross the terminal faces of the fibers and enter the air. Then, in the diverged state, they are passed into the converging lens system 3. Let $P_1$ stand for the focal point of infrared laser beams, $P_2$ for the focal point of visible rays, $a_1$ for the distance from the terminal face of the optical fiber 2 for infrared beams to the center of the converging lens system 3, $a_2$ for the distance from the terminal face of the optical fiber 5 for visible rays to the center of the converging lens system 3, $b_1$ for the distance from the center of the converging lens system 3 to the focal point $P_1$ of infrared laser beams, $b_2$ for the distance from the center of the converging lens system 3 to the focal point $P_2$ of visible rays, $F_1$ for the focus of the converging lens system 3 relative to infrared laser beams, $f_1$ for the focal distance, $F_2$ for the focus of the converging lens system 3 relative to visible rays, and $f_2$ for the focal distance as illustrated in FIG. 2, and the following relations will be derived from the aforementioned formula (1)

$$1/a_1 + 1/b_1 = 1/f_1 \qquad (2)$$

$$1/a_2 + 1/b_2 = 1/f_2 \qquad (3)$$

It is apparent from the formulas (2), (3) that the distances $b_1$ and $b_2$ can be equalized to each other by properly adjusting the distances $a_1$ and $a_2$. In other words, the focal point $P_1$ for infrared laser beams and the focal point $P_2$ for visible rays are caused to assume positions falling in one plane "R" perpendicularly intersecting the optical axis "n" of the converging lens system 3. Generally, the focal distance of the converging lens system 3 is variable with the frequency of light entering the converging lens system. When the light thus entering the lens system is a group of parallel rays, the focal distance and the distance to the focal point become equal. In the device of this invention, however, since the infrared laser beams and the visible rays passing out of the optical fibers have different wavelengths, the distances $b_1$ and $b_2$ do not become equal even when the distances $a_1$ and $a_2$ are equalized to each other. The focal distance $f_1$ of infrared laser beams and the focal distance $f_2$ of visible rays in the converging lens system 3 are automatically determined by the wavelength of infrared laser beams, the wavelength of visible rays, and the configuration of the converging lens system 3 to be used in the device of the invention.

The distances $a_1$ and $a_2$, therefore, are fixed by substituting the focal distances $f_1$ and $f_2$ in the aforementioned formulas (2), (3) and equalizing the distances $b_1$ and $b_2$ to each other. Then the focal distance of infrared laser beams and that of visible rays become equal when the lens system 3 and the optical fiber 2 for infrared laser beams and the optical fibers 5 for visible rays are disposed within the lens barrel in a relationship such that the distances from the center of the lens system 3 to the terminal face of the fiber 2 and the terminal faces of the fibers 5 may assume the values $a_1$, $a_2$.

When the focal point $P_1$ of infrared laser beams and the focal point $P_2$ for visible rays are separated by an equal distance from the converging lens 3 as described above, the operator of the device is allowed to recognize the focal point $P_1$ of infrared laser beams by seeking out the point at which the diameter of the converging column of visible rays is minimized or the luminance of visible rays is maximized. Generally since the focal point $P_2$ of visible rays has decisively higher luminosity than at any other point, it can be easily discerned by unaided eyes. Naturally, this is true even when an ordinary illuminating bulb is used as the visible ray source.

Figure 3:
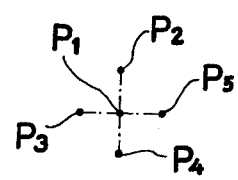
FIG. 3 is an explanatory diagram illustrating the focal points of infrared laser beams and visible rays formed in the laser scalpel device of the present invention.

The embodiment of FIG. 1 has been illustrated as using two optical fibers for the transmission of visible rays. When four optical fibers are used and they are fixed within the lens barrel so that the respective focal points $P_2$, $P_3$, $P_4$, and $P_5$ may be contained in the same plane as the focal point $P_1$ of infrared laser beams and opposed diagonally and equidistantly across the focal point $P_1$ (FIG. 3), the operator is allowed to find the position of the focal point of infrared laser beams not merely in the direction of the advance of infrared laser beams but also with respect to the plane equiangularly intersecting that direction. In this arrangement, therefore, the device offers the advantages that the operator is able to locate the three-dimensional position of the focal point of infrared laser beams with the aid of the focal points of visible rays.

As a material particularly suitable for the optical fiber 2 for the transmission of infrared laser beams, there can be cited KRS-5 (TlBr-TlI). The diameter of this fiber is 0.3 to 1.0 mm. For the transmission of visible rays, those commercially available optical fibers adapted specifically for visible rays and produced in diameters of 0.05 to 0.5 mm can be used in their unmodified form. In the converging lens system 3, a lens made of a material known by the designation ZnSe or KRS-5 can be used. The lens fulfills its function sufficiently with a diameter in the range of 3 to 30 mm. The lens system may be formed of just one lens as illustrated. It may otherwise be formed of two or more lenses. The optical fibers 5 for visible rays may be displaced closely to the optical fiber 2 for infrared laser beams. When the optical system of the laser scalpel device is formed by using the materials described above, the focal points $b_1$, $b_2$ are fixed at a distance of 30 mm and the focal distance of the lens is set to be about 15 mm, for example, the distance $a_1$ becomes about 30 mm and the distance $a_2$ about 15 to 27 mm respectively, though slightly variable with the wavelength of the infrared laser beams and that of the visible rays actually used. By adjusting the distance separating the two types of optical fibers, the distance between the focal point $P_1$ and the focal point $P_2$ can be easily set to the neighborhood of 0.5 mm. The position of the focal point of infrared laser beams, therefore, can be accurately discerned even when only one optical fiber is used for the transmission of visible rays.

As described above, the focal point direct observation type laser scalpel device or laser fabricating device of this invention has a construction wherein the laser beams generated by the infrared laser generator and transmitted through the optical fiber adapted specifically for infrared rays and the visible rays issued by the visible ray source and transmitted through the optical fibers adapted for visible rays are focused by one and the same converging lens system in such a manner that the operator of the device may recognize the focal point of laser beams by seeking the focal point of visible rays. Thus, the device offers the following effects.

(a) Efficient use of the energy of infrared laser beams is ensured because instead of the position of the focus of the converging lens system, the focal point of infrared laser beams which has the highest density of energy is discerned with the aid of the focal point of visible rays.

(b) For the recognition of the focal point of infrared laser beams, the device of this invention depends on the visual observation of the focal point of visible rays unlike the conventional device which makes use of the intersection of two visible rays. Thus, the focal point of visible rays has ample luminosity to be discerned by unaided eyes and the light source for visible rays is not required to impart directivity to the light. Not only a laser of visible rays but also an ordinary visible-ray illuminating lamp or visible-ray emitting diode can be used as the light source.

(c) The device of this invention differs from the conventional device in focusing visible rays and allowing the focal point to be visually observed for the recognition of the focal point of infrared laser beams. The recognition of the focal point of infrared laser beams, therefore, can be obtained even when just one path is used for the transmission of visible rays. Consequently, the converging lens system may be formed by using only one lens. The optical system of the device, therefore, is of a very simple and compact construction.

What is claimed is:

1. A focal point direct observation type laser scalpel device, comprising an infrared laser generator, an optical fiber used for the transmission of an infrared laser beam and connected at one end thereof to said infrared laser generator, a visible ray source, an optical fiber used for the transmission of a visible ray and connected at one end thereof to said visible ray source, and a converging lens system adapted to receive and pass simultaneously an infrared laser beam departing from the other end of said optical fiber for infrared laser beam and a visible ray departing from the other end of said optical fiber for said visible ray, the distance between the other end of said optical fiber for a visible ray and said converging lens system being set to satisfy the condition that the distance between said converging lens system and a focal point of said infrared laser beam is equal to the distance between said converging lens system and a focal point of said visible ray.

2. The laser scalpel device according to claim 1, wherein a plurality of optical fibers are used for the transmission of visible rays.

3. The laser scalpel device according to claim 2, wherein the plurality of optical fibers for visible rays are disposed so that the focal points thereof are equidistant from the focal point of the infrared laser beam.

* * * * *